United States Patent [19]

Schlicht

[11] 4,392,966

[45] Jul. 12, 1983

[54] MOLYBDENUM-ZINC DIALKYLDITHIOPHOSPHATES AS LUBRICANT ADDITIVES

[75] Inventor: Raymond C. Schlicht, Fishkill, N.Y.

[73] Assignee: Texaco Inc., White Plains, N.Y.

[21] Appl. No.: 339,570

[22] Filed: Jan. 15, 1982

[51] Int. Cl.³ .................. C10M 1/54; C10M 1/48
[52] U.S. Cl. ..................... 252/32.7 E; 252/46.6; 260/429.9
[58] Field of Search .............. 260/429.9; 252/327 E, 252/46.6

[56] References Cited

U.S. PATENT DOCUMENTS 3,925,213 12/1975 Froeschmann et al. ....... 252/32.7 E
4,208,292 6/1980 Bridger .......................... 252/32.7 E
4,290,902 9/1981 Levine et al. .................. 252/32.7 E

*Primary Examiner*—Jacqueline V. Howard
*Attorney, Agent, or Firm*—Carl G. Ries; Robert A. Kulason; Henry W. Archer

[57] ABSTRACT

The invention provides molybdenum-zinc dialkyldithiophosphates useful as friction-reducing, anti-wear and oxidation-inhibiting agents in lubricants, in particular, in fuel economy oils.

11 Claims, No Drawings

MOLYBDENUM-ZINC DIALKYLDITHIOPHOSPHATES AS LUBRICANT ADDITIVES

BACKGROUND OF THE INVENTION

Field of the Invention

This invention relates to novel lubricant additives which contain both zinc and molybdenum. It also relates to a lubricant composition which reduces fuel consumption of an internal combustion engine owing to the presence therein of these additives.

DISCUSSION OF THE PRIOR ART

A number of additives already have been suggested and tried in oils to reduce friction in an internal combustion engine thereby allowing a reduction in its energy requirement. Oils so modified are called fuel economy oils.

Heretofore certain molybdenum compounds have been incorporated in oils and greases. The U.S. Pat. No. 3,400,140 describes antiwear agents of the formula

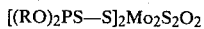

wherein R is hydrocarbyl. U.S. Pat. No. 4,208,292 discloses lube oil additives consisting of phosphomolybdates of the formula:

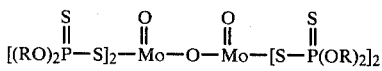

where R is hydrocarbyl. In preparing these compounds the quinquavalent molybdenum atom is reduced with $SO_2$ before reacting it with a dialkyldithiophosphoric acid. Neither of these patents teaches or suggests bimetallic molybdenum-zinc salts of dialkyldithio phosphoric acid nor could their preparative methods produce such compounds.

SUMMARY OF THE INVENTION

The invention provides lubricant additives represented by the generic formula $ZnMo_2O_x[S_2P(OR)_2]_y$ wherein x is 0 to 3; y is 6 to 12; R is a straight-chained or branched hydrocarbyl group having from 3 to 30 carbon atoms or a mixture of at least two such hydrocarbyl groups (a,b,c; etc.) where each group can have values from 1 to 99 molar percents and whose sum must equal 100.

Preferred compounds are those where x is 3, y is 6; R is 2-ethylhexyl; where R is a mixture of 2-ethylhexyl (a); isobutyl (b); and isopropyl (c) in a ratio of a:b:c=about 0.3:0.1:0.6; where R ranges from $C_4$ to $C_8$; a mixture of 4-methyl-2-pentyl (a) and 2-propyl (b) in a ratio of about a:b=0.47:0.53 and a mixture of 4-methyl-2-pentyl (a); 2-methyl-1-propyl (b) and 2-propyl (c) in a molar ratio of about a:b:c=0.32:0.39:29. The invention also provides lubricants containing these additives. Further, the invention provides a method for reducing fuel consumption in an internal combustion engine by treating the moving surfaces thereof with the composition containing the additives of the invention.

DISCLOSURE

The oil-soluble molybdenum/zinc dialkyldithiophosphates of this invention are prepared by zinc metal reduction of a hexavalent molybdic acid or molybdenum salt such as acidified sodium molybdate prior to reaction with sufficient dialkyldithiophosphoric acid to convert both metals to their dialkyldithiophosphate salts. The product is isolated with no attempt to separate the metal salts.

The products of this invention differ from those prepared from non-reduced hexavalent molybdenum in: (1) color: the subject products are brown, while dialkyldithiophosphates prepared from the $Mo^{VI}$ reagent (using the U.S. Pat. No. 3,400,140 procedure) are blue or blue-green; while those prepared according to U.S. Pat. No. 4,208,292 are violet and (2) oil-solubility: the subject compositions, when made from mixed dialkyldithiophosphoric acids which contain high proportions (30–60%) of lower alkyl groups (e.g. isopropyl) are oil-soluble, while the reaction products obtained using the non-reduced $Mo^{VI}$ reagents (as in U.S. Pat. No. 3,400,140) and the same mixed acid possess major amounts of insoluble component(s).

The ability to prepare oil-soluble molybdenum dialkyldithiophosphates containing major amounts of low molecular weight alkyl groups provides advantages in cost and in performance as anti-wear agents and anti-oxidants. The wear-inhibiting properties of zinc dialkyldithiophosphates are known to be inversely related to the molecular weight of the alkyl groups employed.

The preparation of the present products can be represented as follows:

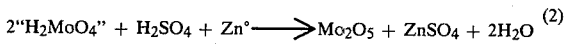

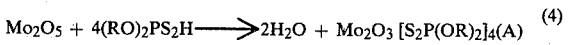

(a)"$H_2MoO_4$" is used to represent the polymolybdic acid mixture formed under the reaction conditions.
(b)A complex mixed salt (C) $ZnMo_2O_3[S_2P(OR)_2]_6$ may also be formed.

The subject process employs the reduction by zinc metal of $Mo^{(VI)}$ to $Mo^{(V)}$ prior to reaction with a dialkyldithio-phosphoric acid, in order to prevent the undesired side reaction of $Mo^{(VI)}$ (a known oxidant) with the acid to form bis-dialkylthiophosphoryl-disulfides and other oxidation products. The side reaction consumes a significant portion of the dialkyldithiophosphoric acid, thus decreasing the conversion to the desired molybdenum dialkyldithiophosphates as well as introducing undesired side-reaction products. Also the reducing agent, zinc, is incorporated into the product and therefore is utilized and not wasted.

Broadly stated, the method of the invention comprises acidifying a hexavalent alkali metal or ammonium molybdate with 3 hydrogen equivalents of mineral acid to form a solution containing a polymolybdic acid mixture; cooling the acidified solution to around ambient temperature; adding finely divided zinc to the solution in a 0.5:1 g. atomic ratio of Zn:Mo; agitating the solution until the hexavalent molybdenum has been reduced; adding 1.0 hydrogen equivalent of base and then 3.0–6.0 moles of a dialkyldithiophosphoric acid; refluxing the mixture and azeotroping to remove the water of reaction. Then the mixture is cooled to ambient temperature; filtered, the filtrate is distilled under reduced pressure and a liquid or solid residue is collected as the useful product.

The dialkyldithiophosphoric acids used in the above synthesis are prepared by the conventional procedure of reacting $P_2S_5$ with four or more moles of the desired alcohol or alcohol mixture at 70°–80° C., in the presence of an inert solvent (usually cyclohexane, n-heptane or other hydrocarbon). The reaction mixture is filtered to remove small amounts of sulfur and unreacted $P_2S_5$, and the filtrate containing the dialkyldithiophosphoric acid is employed in the preparation of the Mo/Zn dialkyldithiophosphate.

Preparation of the subject compositions is illustrated in the following examples which are representative but not limitative of the best mode of carrying out the invention.

EXAMPLE I

This example illustrates the preparation of molybdenum/zinc di-2-ethylhexyldithiophosphate.

A solution of 24.20 g. (0.10 mole) $Na_2MoO_4.2H_2O$ in 50 ml water is stirred while adding 15.0 g (0.15 mole) conc. $H_2SO_4$, the temperature rising from room temperature to a maximum of 60°, cooling being used. When the mixture is cooled to about 30°, 3.63 g. (0.05 g. atom) of zind dust is added over 15 minutes. The temperature rises to about 45°–50° C. The mixture is stirred 4 hrs. at 30°, forming a blue solution and blue solids, the color change indicating that hexavalent molybdenum has been reduced to a lower valence. Next 4.00 g. (0.10 mole) NaOH is added, and the mixture stirred at 50° C., max. for 1 hr. (the color having now turned brown). Thereafter, 25 ml. ethyl acetate and 210 g. of a n-heptane solution containing 0.30 mole of bis-(2-ethylhexyl)-dithiophosphoric acid are added to the reaction flask. The mixture is stirred for ½ hr. at ambient temperature before being heated to the reflux temperature of the solvent mixture. The water is removed by azeotropic distillation into a Dean-Stark trap, recycling the supernatant hydrocarbon distillate back into the reaction flask. A total of 51 ml water was collected after refluxing for 4 hours at 79°–100° C. The mixture is then cooled and filtered, and the filtrate is stripped at reduced pressure ($\sim$10 mm Hg) to 80° C. The yield was 116 g. of a clear, deep brown liquid which had the following analyses: % Mo=7.04, % Zn=2.6, % P=7.5, % S=13.3, and % Na=0.0055. These analyses correspond to atomic ratios of Mo:Zn:P:S=1:0.54:3.30:5.67, which closely approaches the 1:0.5:3:6 ratio calculated for the Mo/Zn dialkyldithiophosphate $ZnMo_2[S_2P(OR)_2]_6$.

EXAMPLE 2

This example illustrates the preparation of a Mo/Zn dialkyldithiophosphate, using a dialkyldithiophosphoric acid prepared from a mixture of higher and lower alcohols.

The procedure of Example 1 was followed, charging the same materials, except for using 168.3 g (0.3 mole) of a heptane solution of a dialkyldithiophosphoric acid prepared from a mixture of 2-ethylhexanol:isobutanol-:isopropanol in a mole ratio of 0.3:0.1:0.6. The product (78 g) was, again, brown and had the following analyses:

|  | Mo | Zn | P | S |
|---|---|---|---|---|
| %, wt | 8.55 | 3.55 | 9.8 | 16.9 |
| At. Ratio | 1 : | 0.61 : | 3.55 : | 5.93 |

The product was completely soluble at 0.93% (wt) in a fully formulated 10W-40 motor oil.

EXAMPLE 3

This example illustrates the preparation of a molybdenum dialkyldithiophosphate as in Ex. 2 with the omission of zinc metal.

A solution of 36.30 g (0.15 mole) $Na_2MoO_4.2H_2O$ in 40 ml. water was treated with an equivalent amount of $H_2SO_4$ (15.00 g.=0.15 mole). Then 168.3 g of a heptane solution containing 0.3 mole of the mixed dialkyldithiophosphoric acid used in Ex. 2 was added, along with 150 ml additional n-heptane and 300 ml. ethyl acetate. After reaction at reflux as in Ex. 1, the stripped product was a mixture of a blue-green liquid and some blue solids. The liquid portion was only partially soluble at 0.5% wt. when added to a commercial SAE 10W-40 motor oil. The color and solubility differences between the products of Ex. 2 and 3 illustrate the uniqueness of the compositions of subject invention.

EXAMPLE 4

This example illustrates the preparation of the Ex. 2 product, without using ethyl acetate.

The procedure of Ex. 2 was followed, using heptane as the primary solvent and adding 12 ml. cyclohexane to depress the initial boiling point to that obtained in Ex. 2 using heptane/ethyl acetate. The other materials were identical to those in Ex. 2 in composition and quantity. The product has the following analyses: % Mo=7.85, % Zn=3.9, % P=10.0, % S=22.6.

The following examples illustrate the preparation of Mo/Zn dialkyldithiophosphates, employing a number of different alcohols or mixtures in the preparation of the dialkyldithio-acid solution. The Ex. 4 procedure was followed except that cyclohexane was omitted.

TABLE I

OTHER Mo/Zn DIALKYLDITHIOPHOSPHATE PREPARATIONS

| Ex. No. | Alcohol(s) | Alcohol Mole Ratio[1] | Analysis of Products | | | |
|---|---|---|---|---|---|---|
|  |  |  | % Mo | % Zn | % P | % S |
| 5 | "Alfol 1214" ($n$-$C_{12}$:$n$-$C_{14}$) | 55:45 | 4.0 | 1.6 | 4.8 | 9.0 |
| 6 | "HCO Alcohol" ($C_4$-$C_8$) 2-Propanol | 60: 40 | 8.11 | 3.46 | 9.84 | 18.9 |
| 7 | 4-Methyl-2-pentanol 2-Propanol | 47: 53 | 11.4 | 3.60 | 10.1 | 18.2 |
| 8 | 4-Methyl-2-pentanol 2-Methyl-1-propanol 2-Propanol | 32: 39: 29 | 9.89 | 3.43 | 12.3 | 19.5 |

[1]Ratio of alcohols charged in the preparation of dialkyldithiophosphoric acid.

The above examples 5–8 demonstrate the applicability of the subject invention to the preparation of Mo/Zn dialkyldithiophosphates from a variety of alcohol mixtures.

The products of the above examples were blended into motor oil compositions and tested by various tests.

Of these, the Bench L-38 Test simulates the engine test environment of Federal Test Method No. 791a, Method 3405.1, and provides a method for studying the copper-lead bearing corrosion characteristics of crankcase oils. In carrying out this test, a journal bearing is rotated in a journal bearing rig, (JBR), which contains a pre-weighed connecting rod bearing along with 500 ml of test oil. The oil is heated to 200° F. and the journal rotated at 1725 rpm for 2 hours, an activator is added and the temperature increased to 305° F. for 22 hrs. The bearings are then removed, cleaned with pentane and reweighed. The difference in weight is then reported as the bearing wt. loss (BWL) in mg. The activator is prepared by grinding 2 g of lead chloride with a motorized mortar and pestle and adding 5 ml. of test oil until a paste forms; an additional 25 ml. of test oil is added and the mixture is ground for 5 minutes. The mixture is then transferred to a beaker using approximately 70 ml. of pentane. The mixture is then added to the JBR using pentane in the transfer. The test duration is 24 hrs, the air flow rate is 1480 ml/minute.

The second test employed was the Four Ball Wear Test described in U.S. Pat. No. 3,384,588 which measures the amount of wear a lubricating oil permits at selected test conditions with and without additives to be tested. The greater amount of wear, the poorer the ability of the test oil composition to prevent such wear. This wear is measured in terms fo millimeter wear scar diameter. This test was run for 1 hour at 1800 rpm/200° F./40 kg load. The friction coefficient was measured at the end of the test when the anti-friction film is fully developed.

The "Small Engine Friction Test" (SEFT) is a single cylinder engine test which measures the frictional characteristics of an oil. The values given in Table II are based on the torque required to motor an engine containing the oil under test. The results of this test have been found to correlate with field experience using a large fleet of cars under varied on-the-road driving conditions as the percentage change in torque correlates with a percent change in fuel economy.

The Bench IIID Test measures the oil thickening tendencies of motor oils under high temperature conditions. The test consists of oxidizing a sample of oil in the presence of air with an iron and copper catalyst at 340° F. After 24, 48 and 72 hours the percent increases in viscosity at 40° C. and milliliters evaporation loss are determined on the oxidized oil. After 24 and 48 hours fresh make-up oil is added to the oxidized oil.

The utility of Mo/Zn dialkyldithiophosphates as multi-purpose additives in lubricating oil formulations is demonstrated in the following Tables II and III. The performance of the subject additives in the tests indicated in the tables show that the additives are extremely effective friction-reducing agents which also impart oxidation, corrosion, and wear-preventative properties to lubricant formulations.

The data in Table II shows that very large reductions in friction are obtained by use of the subject Mo/Zn dialkyldithiophosphates. This effect is observed at very low Mo concentrations, and varies somewhat with the nature of the dialkyldithiophosphate. From Table II it can be seen that, compared to a commercial zinc dialkyldithiophosphate, the subject additives are superior in preventing oxidative thickening of the oil, are equivalent or superior in bearing corrosion, and are superior in anti-wear properties. Surprisingly, the molybdenum dialkyldithiophosphate prepared according to Example 3 (omitting the zinc metal reduction step of Example 2) was not sufficiently soluble at 0.5 weight percent in the base oil to permit evaluation thereof in the evaluation tests and therefore must be considered unsuitable as a lubricant additive. This solubility and hence the performance difference illustrates the novelty and advantage of the subject invention as in Example 2.

The commercial zinc dialkyldithiophosphate used in oil A was prepared from the same mixture of alcohols used in the preparation of the Example 6 product. Comparison of the test results with oils A and E demonstrates the effectiveness of the mixed Mo/Zn salt vs. zinc alone.

TABLE II

SMALL ENGINE FRICTION TEST SCREENING OF Mo/Zn DIALKYLDITHIOPHOSPHATES[1]

| Oil | Metal Dialkyldithiophosphates | | | | | Small Engine Friction Test % Friction Decrease[2] at 280° F. |
|---|---|---|---|---|---|---|
|  | Mo/Zn DTP | | Zn DTP | Total % | | |
|  | Ex. No. | (% Wt) | % Wt | Mo | Zn | |
| A | — | — | 1.40 | — | .15 | 0 ± 2[(2)] |
| B | 1 | (1.10) | 1.10 | .08 | .15 | 13 |
| C | 2 | (.93) | .56 | .08 | .096 | 12.8 |
| D | 2[a] | (.57) | .94 | .05 | .116 | 10.5 |
| E | 6 | (.54) | .90 | .05 | .116 | 19.0 |
| F | 6[a] | (.51) | .90 | .04 | .116 | 27.8 |
| G | 6[a] | (.25) | 1.15 | .02 | .135 | 10.2 |

[1]The subject Mo/Zn DTP's were blended into a conventional 10W-40 motor oil formulation, substituted in part for the commercial zinc dialkyldithiophosphate normally employed at 0.15% Zn. The other additive components were a polybutenylsuccinimide at .08% N + a calcium detergent at .23% Ca + about 12% of an oil concentrate of an olefin copolymer VI improver + 0.1% of an oil concentrate of a polymethacrylate pour depressant + 0.25% of an arylamine antioxidant + 0.15% of an ashless rust inhibitor in a paraffinic base oil.
[2]The mean value of six runs of the reference oil A in the test is used as the base upon which to calculate the effect of the experimental additives.
[a]Repeat preparations of those given in the examples.

TABLE III

OTHER TESTS ON LUBRICATING OILS CONTAINING Mo/Zn DIALKYLDITHIOPHOSPHATES

| Oil No. | Mo/Zn Dialkyldithiophosphate | | | | Commercial, Zinc DTP | | Oil Formulation[2] | Bench IIID Test, 74 Hrs (% Viscosity[3] Increase) | Bench L-38 Test (mg Bearing) (Weight Loss) | 4-Ball Wear Test[4] (mm Scar) (diameter) |
|---|---|---|---|---|---|---|---|---|---|---|
|  | Ex. No. | % Wt | % Mo | % P | % Wt | % P |  |  |  |  |
| H | Control | — | — | — | .75 | .08 | 10W-40 | Too Viscous to measure | 31.3 | .45 |
| I | 1 | 1.10 | .08 | .08 | — | — | 10W-40 | 55 | 32.6 | .36 |
| J | 2 | .93 | .08 | .09 | — | — | 10W-40 | 66 | 16.4 | .36 |

TABLE III-continued
OTHER TESTS ON LUBRICATING OILS CONTAINING Mo/Zn DIALKYLDITHIOPHOSPHATES

| Oil No. | Ex. No. | Mo/Zn Dialkyldithiophosphate Conc. in Oil | | | Commercial, Zinc DTP | | Oil Formulation[2] | Bench IIID Test, 74 Hrs (% Viscosity[3] Increase) | Bench L-38 Test (mg Bearing) (Weight Loss) | 4-Ball Wear Test[4] (mm Scar) (diameter) |
|---|---|---|---|---|---|---|---|---|---|---|
| | | % Wt | % Mo | % P | % Wt | % P | | | | |
| K | 6 | .88 | .08 | .09 | — | — | 10W-40 | 71 | 14.9 | .36 |

[1]Zinc dialkyldithiophosphate prepared from the alcohol mixture used in the preparation of Ex. 6 (blend 4).
[2]The test oils differ from a commercial 10W-40 formulation only in the dosage and/or type of metal dialkyldithiophosphate. The other additive components are a polybutenylsuccinimide at .08% N + a calcium detergent at .23% Ca + about 12% of an oil concentrate of an olefin copolymer VI improver + 0.1% of an oil concentrate of a polymethacrylate pour depressant + 0.25% of an aryl amine anti-oxidant + 0.15% of an ashless rust inhibitor in a paraffinic base oil.
[3]Viscosity (kinematic) measured at 100° F.
[4]The 4-Ball Wear Test was run 1 hr at 1800 rpm and 40 kg load at 200° F.

Lubricating compositions according to the present invention contain at least one of the above products in an amount ranging from about 0.1 to 15 percent; preferably between 0.5 and 2.0 percent by weight, and, especially at least 0.5 percent by weight.

The present compositions can also contain a combination of other well-known additives in an amount sufficient to achieve each additive's function.

Lubricating compositions according to this invention comprise a major amount of any of the well-known types of oils of lubricating viscosity as suitable base oils. They include hydrocarbon or mineral lubricating oils of naphthenic, paraffinic and mixed naphthenic and paraffinic types. Such oils may be refined by any of the conventional methods such as solvent refining and acid refining. Synthetic hydrocarbon oils of the alkylene polymer type or those derived from coal and shale may also be employed.

Alkylene oxide polymers and their derivatives such as the propylene oxide polymers and their ethers and esters in which the terminal hydroxyl groups have been modified, are also suitable. Synthetic oils of the dicarboxylic acid ester type including dibutyl adipate, di-2-ethylhexyl sebacate, dilauryl azelate, and the like may be used. Alkyl benzene types of synthetic oils such as tetradecyl benzene, etc., are also included.

What is claimed is:

1. An oil soluble lubricant additive having the generic formula:

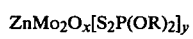

$$ZnMo_2O_x[S_2P(OR)_2]_y$$

wherein x=0–3; y=6 to 12 and R is a straight-chained or branched hydrocarbyl group having from 3 to 30 carbon atoms or a mixture of at least two such hydrocarbyl groups where each group can have values ranging from 1 to 99 molar percents and whose sum equals 100.

2. The lubricant additive of claim 1, wherein R is 2-ethylhexyl, x=3 and y=6.

3. The lubricant additive of claim 1 wherein R represents a mixture of hydrocarbyl groups wherein 2-ethylhexyl: (a) isobutyl: (b) isopropyl (c) are present in a ratio of a:b:c=about 30:10:60 and x=3 and y=6.

4. The additive of claim 1 wherein R represents a mixture of $nC_{12}$ (a) to $nC_{14}$ (b) groups where a:b=about 1:1, and x=3 and y=6.

5. The additive of claim 1 wherein R represents $C_4$ to $C_8$ groups.

6. The additive of claim 1 wherein R represents a mixture of 4-methyl-2-pentyl (a) and 2-propyl (b) groups in a ratio of a:b=about 47:53, and x=3 and y=6.

7. The additive of claim 1 wherein R represents a mixture of 4-methyl-2-pentyl; (a) 2-methyl-1-propyl (b) and 2-propyl (c) in a ratio of a:b:c=about 32:39:29, and x=3 and y=6.

8. A lubricant composition comprising a major amount of an oil of lubricating viscosity and a minor amount of the additive of claim 1 at concentrations of about 0.1 to about 15.0 weight percent.

9. The composition of claim 8 containing from about 0.5 to about 2.0 weight percent of said additive.

10. A method for reducing the fuel consumption of an internal combustion engine which comprises treating the moving surfaces thereof by using a lubricant of the composition of claim 8.

11. A process for preparing molybdenum/zinc dialkyldithiophosphates comprising reducing with zinc metal a hexavalent molybdic acid and/or acified molybdenum salt solution; reacting the zinc and molybdenum intermediate species thus formed with sufficient dialkyldithiophosphoric acid to convert both metals to their dialkyldithiophosphate salts and isolating the product without separating said salts.

* * * * *